(12) United States Patent
Stotts et al.

(10) Patent No.: US 8,489,205 B2
(45) Date of Patent: Jul. 16, 2013

(54) SYSTEM FOR TEMPORARY FIXATION OF AN IMPLANTABLE MEDICAL DEVICE

(75) Inventors: Larry Stotts, Tigard, OR (US); Dirk Muessig, West Linn, OR (US)

(73) Assignee: BioTronik SE & Co. KG, Berlin (DE)

( * ) Notice: Subject to any disclaimer, the term of this patent is extended or adjusted under 35 U.S.C. 154(b) by 0 days.

(21) Appl. No.: 13/455,137

(22) Filed: Apr. 25, 2012

(65) Prior Publication Data

US 2012/0283796 A1    Nov. 8, 2012

Related U.S. Application Data

(60) Provisional application No. 61/481,757, filed on May 3, 2011.

(51) Int. Cl.
     *A61N 1/05*        (2006.01)
(52) U.S. Cl.
     USPC .......................................... 607/126; 607/130
(58) Field of Classification Search
     USPC ......................................... 607/121, 126–132
     See application file for complete search history.

(56) References Cited

U.S. PATENT DOCUMENTS

| | | | | |
|---|---|---|---|---|
| 5,231,986 | A | * | 8/1993 | Bennett ........................ 607/11 |
| 7,082,336 | B2 | * | 7/2006 | Ransbury et al. ........... 607/126 |
| 7,725,197 | B2 | * | 5/2010 | Soltis et al. ................ 607/129 |

FOREIGN PATENT DOCUMENTS

| | | |
|---|---|---|
| EP | 2184082 A1 | 5/2010 |
| WO | 2007/092330 A1 | 8/2007 |
| WO | 2008/144319 A1 | 11/2008 |
| WO | 2010/144016 A1 | 12/2010 |

OTHER PUBLICATIONS

European Search Report dated Aug. 28, 2012, 6 pages.

* cited by examiner

*Primary Examiner* — Brian T Gedeon
(74) *Attorney, Agent, or Firm* — ARC IP Law, PC; Joseph J. Mayo

(57) ABSTRACT

A medical fixation system for temporary fixation of an implantable medical device such as a short lead pacemaker outside of the heart in a larger blood vessel such as the superior or inferior vena cava. The fixation mechanism or element is temporary in nature in that the fixation holds the implantable medical device in place until the implantable medical device is grown in to the wall of the vessel and the short lead attached to the implantable medical device and implanted in the heart is grown in. The cell tissue surrounding the implantable medical device and the short lead then keeps the implantable medical device in place without the temporary fixation element.

20 Claims, 5 Drawing Sheets

PRIOR ART

PRIOR ART

US 8,489,205 B2

SYSTEM FOR TEMPORARY FIXATION OF AN IMPLANTABLE MEDICAL DEVICE

This application claims the benefit of U.S. Provisional Patent Application 61/481,757 filed on 3 May 2011, the specification of which is hereby incorporated herein by reference.

BACKGROUND OF THE INVENTION

1. Field of the Invention

Embodiments of the invention relate to a medical fixation device. More particularly, but not by way of limitation, at least one embodiment enables a system for temporary fixation of an implantable medical device such as a short lead pacemaker outside of the heart and in a large blood vessel such as the inferior vena cava. The fixation mechanism or element is temporary in nature in that the fixation holds the implantable medical device in place until the implantable medical device is grown in to the wall of the vessel and the short lead attached to the implantable medical device and implanted in the heart is grown in. The cell tissue surrounding the implantable medical device and the short lead then keeps the implantable medical device in place without the temporary fixation element.

2. Description of the Related Art

Traditional cardiac rhythm management or CRM devices include medical devices that are usually implantable and permanently connected to electrode leads for delivery of electrical stimulations pulses to the tissue or myocardium of a human heart. Typically, the electrodes are coupled to the myocardium through intravenous or epicardial leads, so that the housing of the pacemaker may be placed remotely to the heart. This type of pacemaker is shown in FIG. 1 that specifically illustrates a three chamber pacemaker 10 connected to pacing/sensing leads placed in a heart 12. The pacemaker 10 is coupled to the heart 12 by way of leads 14, 16 and 30.

Lead 14 is implemented with a pair of right atrial electrodes 18 and 20 that are in contact with the right atria of the heart 12, and the lead 16 implemented with a pair of electrodes 22 and 24 that are in contact with the right ventricle 28 of heart 12. The electrodes 18 and 22 are tip-electrodes at the very distal end of leads 14 and 16, respectively. Electrodes 20 and 24 are implemented as ring electrodes in close proximity but electrically isolated from the respective tip electrodes 18 and 22. Also shown is electrode lead 30 that includes a left ventricular tip electrode 32 at the distal end.

Presently the CRM device industry is investigating new products called "leadless pacemakers". These leadless devices minimize potential lead breakages and pocket infections. Based on technology advances of integrated circuits and batteries, implantable pacemakers can be built so small that the entire device may be implanted directly into the heart. Depending on the place of implant, for example atrium or ventricle, and the size of the heart chamber relative to the length of the leadless pacemaker, one potential problem is that the pacemaker may touch the cardiac valve, which separates the atrium form the ventricle. If the pacemaker touches the cardiac valve, blood regurgitation may occur. Another problem relates to the size limitations of these types of leadless pacemakers wherein based on the small size, the pacemakers may be limited in their functionality. For example, due to size constraints, small pacemakers may not provide statistics of detected cardiac events or wireless telemetry. An example "leadless" pacemaker is shown in FIG. 2. As shown when pulse generator 10' senses electrical activity from right ventricular electrode 22 for example, the pulse generator 10' sends an ultrasonic pulse to wireless electrode 32', which powers and/or otherwise causes a pace event in the left ventricle.

For at least the limitations described above with respect to leadless pacemakers, there is a need for a system for temporary fixation of an implantable medical device such as a short lead pacemaker in a large blood vessel such as the inferior vena cava.

BRIEF SUMMARY OF THE INVENTION

At least one embodiment of the invention solves the problems associated with leadless pacemakers through temporary fixation of the actual pacemaker in the large vessel feeding blood to the right side of the heart, which is known as the vena cava. This placement allows a larger device to be utilized with respect to a leadless pacemaker implanted inside the heart, wherein the larger pacemaker may therefore include more features and functionality. This type of larger device is temporarily fixated in the vessel until it is grown in to the wall of the vessel and the very short lead that is implanted in the heart is fully grown in. Once grown in, the fixation mechanism is not needed anymore. The temporary nature of the fixation enables later explantation, for example to replace a battery due to battery depletion.

One major drawback of known solutions for fixation of implantable medical devices in a large blood vessel is that the fixation mechanism or element needs to be cut for device removal or is highly complex.

At least one embodiment of the invention provides fixation for an implantable device within a blood vessel that fixes the position of the implantable device temporarily and disappears or dissolves after a predefined time or after being exposed to an external chemical or physical stimulus.

In one embodiment the implantable device comprises a lead that is relatively short compared to a conventional pacemaker lead. In other embodiments, the implantable device is connected to a lead for implantation in the heart, wherein the lead is relatively short. The lead is moved by a steerable catheter through a blood vessel into the heart. The lead is fixated in the heart after implantation as known in the art. The implantable device housing, containing the electronics and battery, remains in the blood vessel and has one or more fixation mechanisms or elements attached to it. In an alternative embodiment, first the lead is implanted and fixated and then after the lead is fixated, the implantable device is implanted by a steerable catheter through a blood vessel and connected to the lead. Once the lead is implanted in the heart and fixated and the implantable device is connected to the lead and in its desired position, the fixation mechanism or element of the implantable device is engaged to temporarily fix the implantable device at or against the blood vessel wall and therefore hold it in place. In one embodiment, the steerable catheter provides for a mechanism to engage the fixation mechanism or element. In another embodiment, the fixation mechanism is engaged by moving the device back. In yet another embodiment, the fixation mechanism or element is self-engaging after a defined period of time. In yet another embodiment, the fixation mechanism or element is engaging in response to an external chemical or physical stimulus.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A system for temporary fixation of an implantable medical device will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 3:
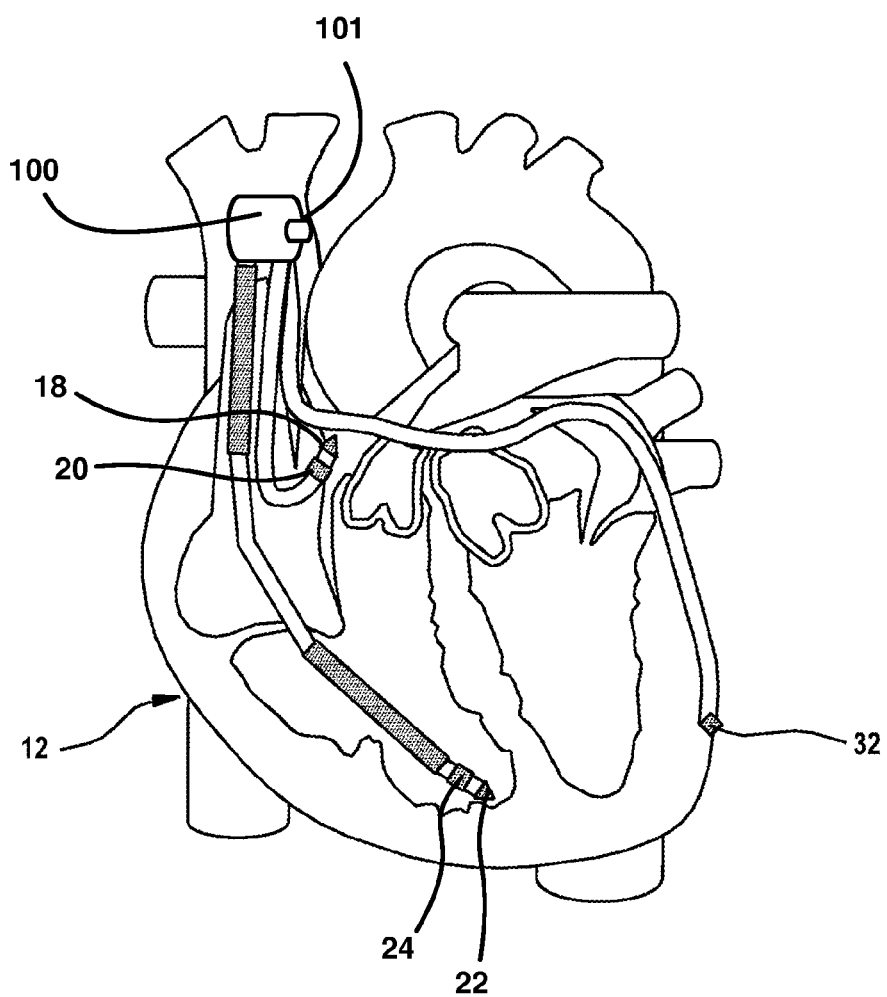
FIG. 3 illustrates a view of an embodiment of the invention including short lead pacemaker and temporary fixation element.

FIG. 3 illustrates a view of an embodiment of the invention. As shown pacemaker 100 is implanted within the vena cava. Embodiments of the invention may be implanted in any portion of the vena cava as desired including the superior vena cava or inferior vena cava. Temporary fixation element 101 is shown coupling implant 100 to the interior portion of the vena cava. Although the lead that extends to the right ventricle shows two extended shock elements, these are optional and may be utilized or not in keeping with the spirit of the invention.

Figure 2:
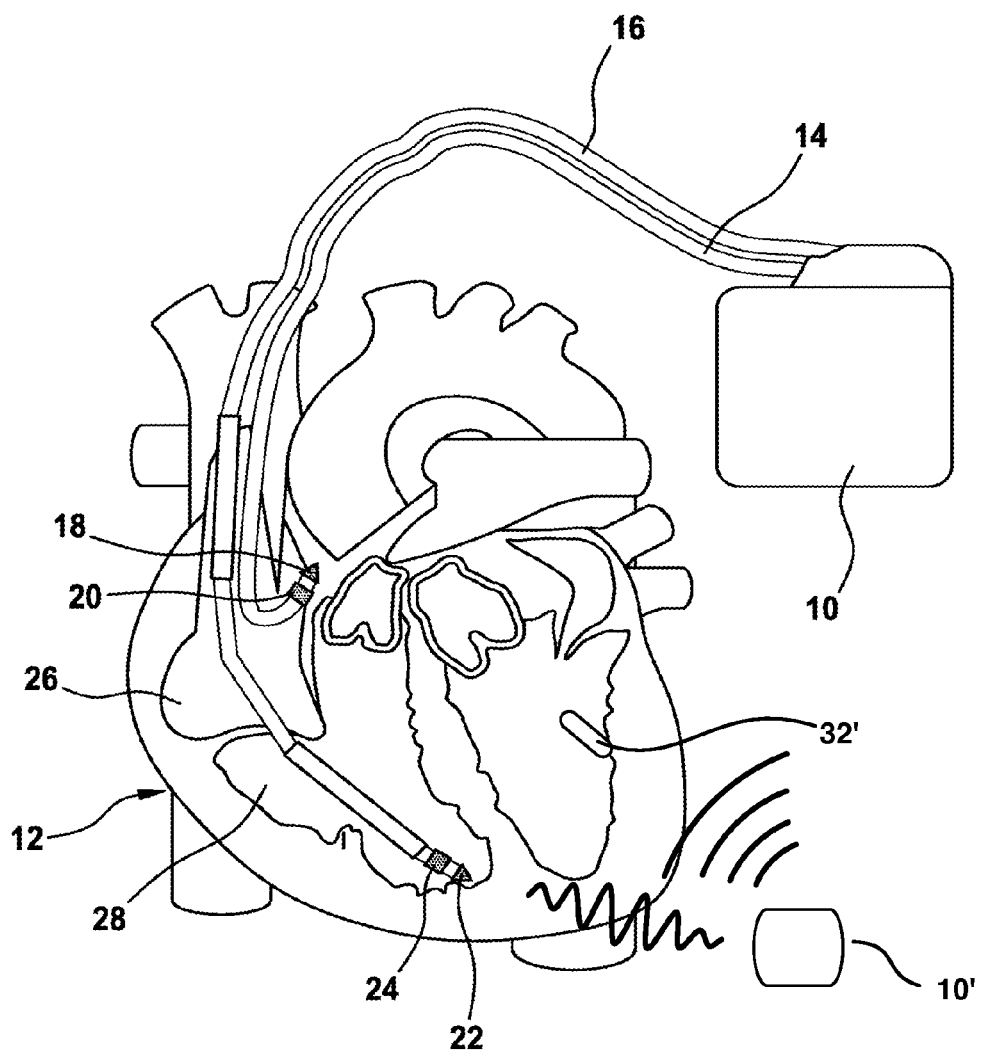
FIG. 2 illustrates a view of a leadless pacemaker.
Figure 4:
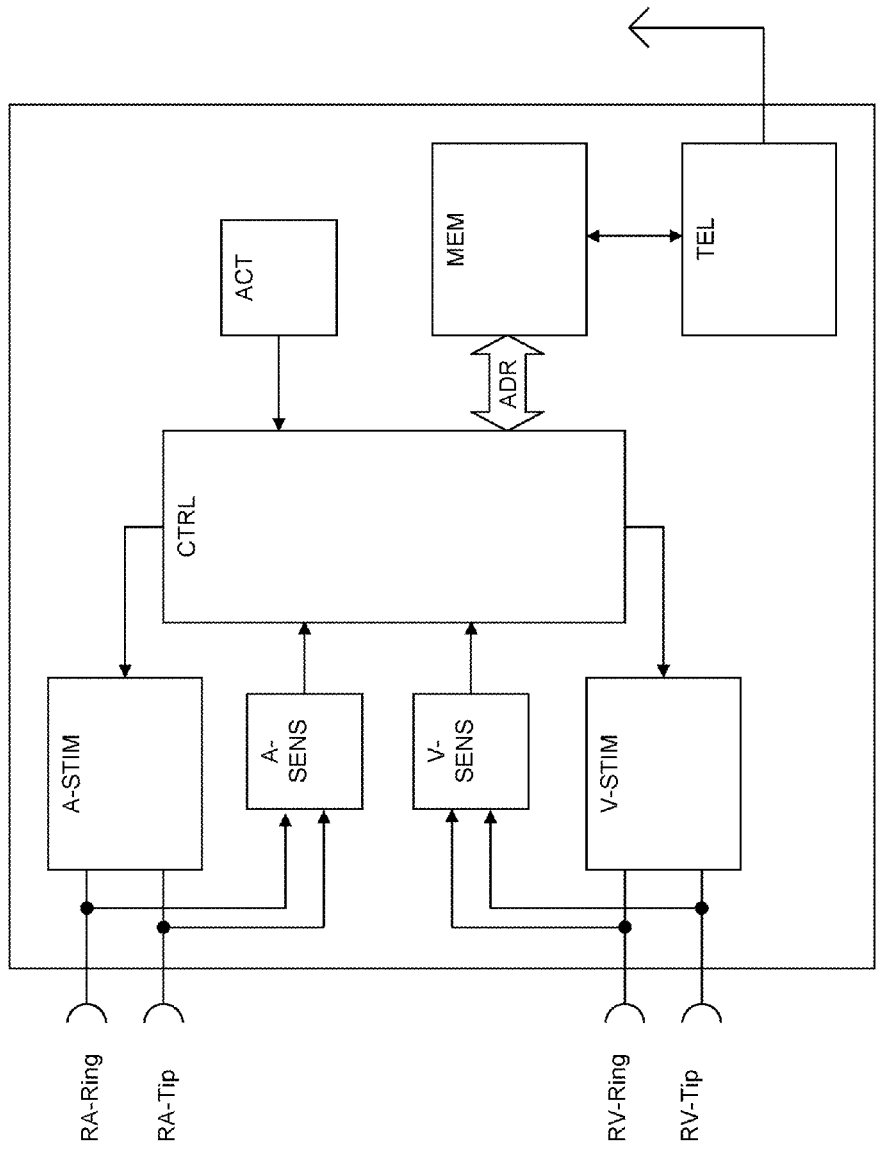
FIG. 4 illustrates the internal components of a pacemaker in accordance with at least one embodiment of the invention.

FIG. 4 illustrates the internal components of a pacemaker in accordance with at least one embodiment of the invention. As shown in this simplified block diagram representative of a basic version of pacemaker 100 for example, right atrial ring and tip electrodes, RA-Ring and RA-Tip, couple with atrial stimulation and sensing elements, A-STIM and A-SENS. The right ventricle ring and tip electrodes, RV-Ring and RV-Tip couple with the ventricular stimulation and sensing elements, V-STIM and V-SENS. Not shown for brevity are left atrial and left ventricular stimulation and sensing elements, which may also be employed as desired. The right and left atrial and/or ventricular elements are coupled with the control unit, CNTL. Since pacemaker 100 may be implemented in a larger format than wireless lead 32', activity element ACT, memory MEM via address buss ADR, and telemetry TEL may also be coupled with the control unit and hence included within pacemaker 100. Generally, these elements are not utilized with leadless pacemakers and wireless electrodes, such as wireless electrode 32' as shown in FIG. 2 for example since communication to the wireless lead is one way and hence there is no manner in which to obtain data from wireless lead 32' even if the wireless electrode was able to store this type of data.

Figure 1:
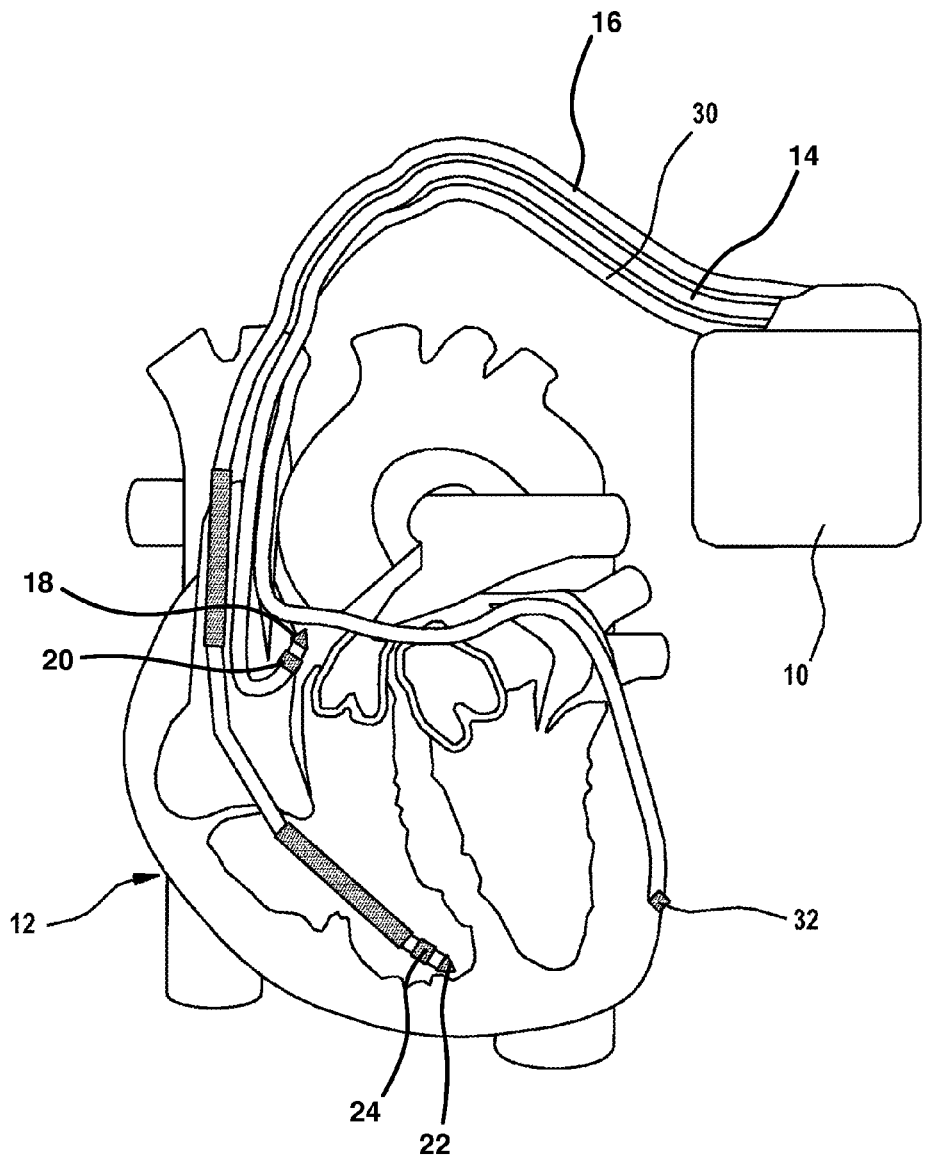
FIG. 1 illustrates a view of a traditional pacemaker and leads.
Figure 5:
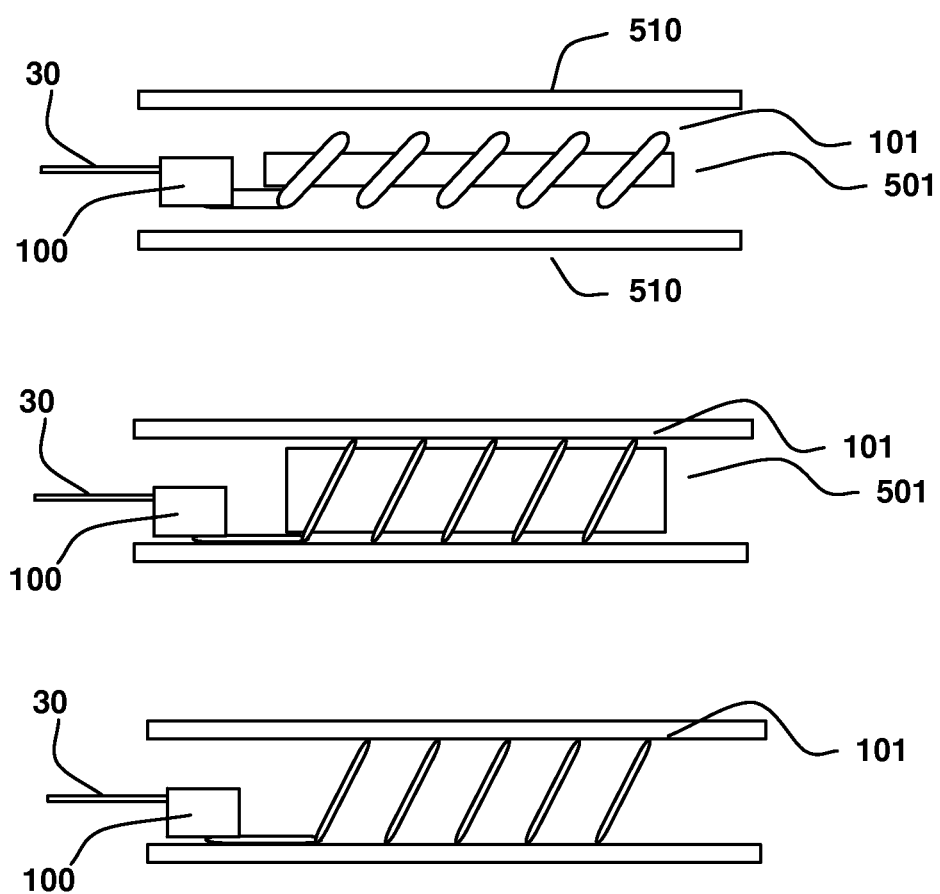
FIG. 5 illustrates an embodiment of the temporary fixation element.

FIG. 5 illustrates an embodiment of the temporary fixation element 101 as shown in FIG. 1. In one particular embodiment the implantable device comprises lead 30, for example a left ventricle lead or is connected a lead for implantation in the heart. The implantable device 100 with the lead is mounted for implantation on a steerable catheter that allows placement of the lead of the implantable device in a vein near the heart, which is shown as the outer two parallel lines 510.

The device housing of implantable device 100, containing the electronics and battery, remains in the blood vessel for example vein 510 and may include at least one stent-like fixation mechanism or element attached to it, or utilize any other type of coupling to the vein, so long as it may be uncoupled when desired. The steerable catheter runs through the inner lumen of the stent-like fixation mechanism or element and provides one or more balloons 501 capable of extending the stent-like fixation mechanism or element. Once the lead of the device is implanted in the heart and adequate sensing and pacing is ensured, balloon 501 is inflated as is shown in the middle sub-figure, extending the stent-like fixation mechanism or element against the vessel wall and therefore holding it in place after the balloon is deflated and removed, hence fixing the implantable device housing 100 to vein 510.

After four to six weeks the implantable device housing 100 and pacing lead 30 extending into the heart are fully grown in, and fully support the fixation of the implantable device housing 100. At that time the fixation mechanism or element 501 does not to be utilized to hold the implantable device housing in place since the tissue encapsulating the device and the pacing lead support the implantable device securely.

In one embodiment, a biodegradable material e.g. a magnesium based alloy is used for the fixation mechanism or element 101. The properties of the magnesium based alloy are selected such, that fixation mechanism or element dissolves after a defined period of time. In one embodiment, the fixation mechanism or element dissolves after a period of four to six weeks.

In an alternative embodiment, the material of the fixation mechanism or element is a material that dissolves when exposed to an external stimulus. In one embodiment, chemical stimuli, such as a change in the pH value, caused by supplying a weak acid or by causing an inflammatory reaction, may be utilized. Polymers, which, for example, are composed of acrylic acid, methacrylic acid, maleic anhydride, or N,N-dimethylaminoethyl-methacrylate, respond with sensitivity to a pH change and may be utilized as suitable materials for the fixation mechanism or element. In another embodiment the external stimulus is of a physical stimulus, such as a change in the temperature or exposition to electromagnetic radiation. A material that dissolves when exposed to such a physical stimulus may be also be utilized as a suitable material for the fixation mechanism or element. Examples are materials that comprise thermoresponsive polymers like polymers which can be synthesized from the following monomers: N-isopropylacrylamide, N,N-diethylacrylamide, methyl vinyl ether, N-vinylcaprolactam, and ethylene oxide-co-propylene oxide. The list of substances provided here is not exhaustive. One skilled in the art will appreciate that substances having similar properties removable or temporary properties may also be utilized in keeping with the spirit of the invention.

To avoid irritations of the implantable device, the device housing as well as the fixation mechanism or element may be coated with inflammatory suppressing drugs.

While the invention herein disclosed has been described by means of specific embodiments and applications thereof, numerous modifications and variations could be made thereto by those skilled in the art without departing from the scope of the invention set forth in the claims.

What is claimed is:

1. A system for temporary fixation of an implantable medical device comprising:

at least one electrical lead configured to be implanted in a heart and grow in after implantation;

a housing coupled with said at least one electrical lead wherein said housing is configured to be implanted within a blood vessel wherein said housing comprises
- at least one stimulation pulse generator to selectively generate stimulation pulses to the heart via said at least one electrical lead;
- at least one sensing stage configured to process electrical signals from the heart via said at least one electrode lead;
- a control unit connected to said at least one stimulation pulse generator and to said at least one sensing stage;
a temporary fixation element configured to couple said housing with an internal portion of said blood vessel until said at least the implantable medical device or one electrical lead has grown in; and,
wherein said temporary fixation element is configured to dissolve after exposed to an externally supplied stimulus.

2. The system according to claim 1 wherein said at least one electrical lead is configured to fix said housing to said heart after said temporary fixation element is uncoupled from said housing.

3. The system according to claim 1, wherein said housing further comprises a telemetry unit coupled with said control unit.

4. The system according to claim 1, wherein said housing further comprises an activity unit coupled with said control unit.

5. The system according to claim 1, wherein said housing further comprises a memory coupled with said control unit.

6. The system according to claim 1 wherein said temporary fixation element is configured to dissolve after a predefined time.

7. The system according to claim 1 wherein said temporary fixation element comprises a magnesium based alloy that is configured to dissolve after four to six weeks.

8. The system according to claim 1 wherein said externally supplied stimulus is an externally supplied chemical stimulus.

9. The system according to claim 1 wherein said externally supplied stimulus is an externally supplied chemical stimulus and wherein said temporary fixation element comprises acrylic acid, methacrylic acid, maleic anhydride, or N,N-dimethylaminoethyl-methacrylate.

10. The system according to claim 1 wherein said externally supplied stimulus is an external physical stimulus, wherein the external physical stimulus comprises one or more of a physical external stimulus that causes a change in the temperature or exposition to electromagnetic radiation.

11. The system according to claim 1 wherein said externally supplied stimulus is an external physical stimulus and wherein said temporary fixation element comprises at least one thermoresponsive polymer synthesized from one or more of the following monomers: N-isopropylacrylamide, N,N-diethylacrylamide, methyl vinyl ether, N-vinylcaprolactam, and ethylene oxide-co-propylene oxide, and wherein the external physical stimulus comprises one or more of a physical external stimulus that causes a change in the temperature or exposition to electromagnetic radiation.

12. The system according to claim 1 wherein said temporary fixation element and said housing comprise a coating comprising an inflammatory suppressing drug.

13. A system for temporary fixation of an implantable medical device comprising:
- at least one electrical lead configured to be implanted in a heart and grow in after implantation;
- a housing coupled with said at least one electrical lead wherein said housing is configured to be implanted within a vein wherein said housing comprises
  - at least one stimulation pulse generator to selectively generate stimulation pulses to the heart via said at least one electrical lead;
  - at least one sensing stage configured to process electrical signals from the heart via said at least one electrode lead;
  - a control unit connected to said at least one stimulation pulse generator and to said at least one sensing stage;
  - a memory coupled with said control unit;
- a temporary fixation element configured to couple said housing with an internal portion of a vein until said at least the implantable medical device or one electrical lead has grown in;
- wherein said at least one electrical lead is configured to fix said housing to said heart after said temporary fixation element is uncoupled from said housing; and,
- wherein said temporary fixation element is configured to dissolve after exposed to an externally supplied stimulus.

14. The system according to claim 13, wherein said housing further comprises a telemetry unit coupled with said control unit.

15. The system according to claim 13, wherein said housing further comprises an activity unit coupled with said control unit.

16. The system according to claim 13 wherein said temporary fixation element is configured to dissolve after a predefined time.

17. The system according to claim 13 wherein said temporary fixation element comprises a magnesium based alloy that is configured to dissolve after four to six weeks.

18. The system according to claim 13 wherein said external stimulus is an externally supplied chemical stimulus.

19. The system according to claim 13 wherein said external stimulus is an externally supplied chemical stimulus and wherein said temporary fixation element comprises acrylic acid, methacrylic acid, maleic anhydride, or N,N-dimethylaminoethyl-methacrylate.

20. The system according to claim 13 wherein said temporary fixation element and said housing comprise a coating comprising an inflammatory suppressing drug.

* * * * *